United States Patent
Cahill et al.

(10) Patent No.: US 7,706,617 B2
(45) Date of Patent: Apr. 27, 2010

(54) IMAGE INDEXER FOR INDEXING A PLURALITY OF IMAGES

(75) Inventors: Nathan D. Cahill, West Henrietta, NY (US); Marvin M. Goodgame, Ontario, NY (US); Shoupu Chen, Rochester, NY (US); Lawrence A. Ray, Rochester, NY (US)

(73) Assignee: Carestream Health, Inc., Rochester, NY (US)

( * ) Notice: Subject to any disclaimer, the term of this patent is extended or adjusted under 35 U.S.C. 154(b) by 628 days.

(21) Appl. No.: 11/097,932

(22) Filed: Mar. 30, 2005

(65) Prior Publication Data
US 2006/0239557 A1 Oct. 26, 2006

(51) Int. Cl.
*G06K 9/00* (2006.01)
(52) U.S. Cl. ............... 382/224; 382/181; 382/225; 382/226; 382/227; 707/6
(58) Field of Classification Search ......... 382/225–227, 382/181; 707/6
See application file for complete search history.

(56) References Cited

U.S. PATENT DOCUMENTS

| 4,176,953 | A | * | 12/1979 | Bartoov et al. ............. 356/73 |
| 5,704,531 | A | | 1/1998 | Nam ............... 224/676 |
| 5,943,443 | A | * | 8/1999 | Itonori et al. ............ 382/225 |
| 7,139,607 | B1 | * | 11/2006 | Shelchuk ............... 607/9 |

OTHER PUBLICATIONS

U.S. Appl. No. 10/812,785, filed Mar. 30, 2004, Nathan D. Cahill et al.
U.S. Appl. No. 10/175,148, filed Jun. 20, 2002, Glukhovsky et al.
U.S. Appl. No. 10/150,018, filed May 20, 2002, Frisch et al.
"Global Optimization Techniques and Applications" by Nathan D. Cahill. Master's Thesis, Rochester Institute of Technology, May 2000.
"Optimization by Simulated Annealing" by Kirkpatrick, Gelatt, and Vecchi. *Science*, 220(4598): 671-680, May 13, 1983.
"Thermodynamcial Approach to the Travelling Salesman Problem: An Efficient Simulation Algorithm" by Cerny. *J. Opt. Theo. Applns.*, 45:41-51, 1985.

(Continued)

*Primary Examiner*—Charles Kim
*Assistant Examiner*—John W Lee

(57) ABSTRACT

An image indexer for indexing a plurality of images that includes a first data structure for subsequent classification of the one or more images. The first data structure includes characteristics for at least one class. An image classifier classifies one or more individual images found in the plurality of images as classified images according to the first data structure. A second data structure performs subsequent clustering of the plurality of images, wherein the second data structure includes at least two sequential events in a set of known events. The classified images are clustered according to the second data structure, and a representative image is selected from each cluster of classified images.

13 Claims, 8 Drawing Sheets

OTHER PUBLICATIONS

"Equation of State Calculations by Fast Computing Machines" by Metropolis, Rosenbluth, Rosenbluth, Teller, and Teller. *J. Chem. Phys.*, 21:1087-1092, 1953.

"Optimization by Simulated Annealing: An Experimental Evaluation- Part I (Graph Partitioning)" by Johnson et al. *Operations Research*, 37:865-892, 1989.

"Simulated Annealing: An Introduction" by Aarts and van Laarhoven. *Statistical Neerlandica*, 43(1): 31-52, 1989.

"Capacitated Clustering Problems by Hybrid Simulated Annealing and Tabu Search" by Osman and Christofides. Int. Trans. Opera. Res., 1:317-337, 1994.

\* cited by examiner

IMAGE INDEXER FOR INDEXING A PLURALITY OF IMAGES

FIELD OF THE INVENTION

The present invention relates generally to an in vivo camera system and, in particular, to indexing sequences of images captured by an in vivo camera system according to anatomical structure.

BACKGROUND OF THE INVENTION

Several in vivo measurement systems are known in the art. They include swallowable electronic capsules which collect data and which transmit the data to a receiver system. These intestinal capsules, which are moved through the digestive system by the action of peristalsis, are used to measure pH ("Heidelberg" capsules), temperature ("CoreTemp" capsules) and pressure throughout the gastro-intestinal (GI) tract. They have also been used to measure gastric residence time, which is the time it takes for food to pass through the stomach and intestines. These intestinal capsules typically include a measuring system and a transmission system, where a transmitter transmits the measured data at radio frequencies to a receiver system.

U.S. Pat. No. 5,704,531, assigned to the State of Israel, Ministry of Defense, Armament Development Authority, and incorporated herein by reference, teaches an in vivo measurement system, in particular an in vivo camera system, which is carried by a swallowable capsule. In addition to the camera system there is an optical system for imaging an area of the GI tract onto the imager and a transmitter for transmitting the video output of the camera system. The overall system, including a capsule that can pass through the entire digestive tract, operates as an autonomous video endoscope. It also images the difficult to reach areas of the small intestine.

FIG. 1 shows a block diagram of the in vivo video camera system described in U.S. Pat. No. 5,704,531. The system captures and transmits images of the GI tract while passing through the gastro-intestinal lumen. The system contains a storage unit 100, a data processor 102, a camera 104, an image transmitter 106, an image receiver 108, which usually includes an antenna array, and an image monitor 110. Storage unit 100, data processor 102, image monitor 110, and image receiver 108 are located outside the patient's body. Camera 104, as it transits the GI tract, is in communication with image transmitter 106 located in capsule 112 and image receiver 108 located outside the body. Data processor 102 transfers frame data to and from storage unit 100 while analyzing the data. Processor 102 also transmits the analyzed data to image monitor 110 where a physician views it. The data can be viewed in real time or at some later date.

During a typical examination, the in vivo camera system may take anywhere from about four to eight hours or more to traverse the digestive tract. Assuming a capture rate of about 2 images per second, the total number of captured images can range from approximately 35,000 to 70,000 or more images. If these images were subsequently displayed as a video sequence at a rate of 30 frames per second, one would require 20-40 minutes of viewing time to observe the entire video. This estimate does not include the extra time needed to zoom in and/or decrease the frame rate for a more detailed examination of suspect areas.

In many situations, the physician may desire to navigate the video by jumping from one anatomical structure to another anatomical structure, rather than cueing and rewinding the video manually. This type of navigation is simplified when the video sequence is indexed according to anatomical structure. The indexing process entails establishing a set of key frames that are representative of certain anatomical structures of interest. Commonly assigned U.S. patent application Ser. No. 10/812,785, incorporated herein by reference, describes a method and system for identifying the anatomical structure corresponding to an in vivo image, based on the classification of image based and/or non-image based features of the in vivo image. The disclosure of patent application '785 reveals a rudimentary indexing system. For example, one may select the first in vivo images in the sequence as key frames that are classified according to each anatomical structure of interest. However, there remains a need in the art for indexing in vivo image sequences according to anatomical structure, in a way that is robust to the misclassification of individual in vivo images.

SUMMARY OF THE INVENTION

The present invention is directed to overcoming one or more of the problems set forth above. Briefly summarized, according to one aspect of the present invention, an indexing system that is robust to misclassification errors is provided in the form of an image indexer for indexing a plurality of images, comprising the steps of: providing a first data structure for subsequent classification of the one or more images, wherein the first data structure includes characteristics for at least one class; classifying, according to the first data structure, one or more individual images found in the plurality of images as classified images; providing a second data structure for subsequent clustering of the plurality of images, wherein the second data structure includes at least two sequential events in a set of known events; clustering the classified images according to the second data structure; and selecting for each cluster of classified images, a representative image.

These and other aspects, features and advantages of the present invention will be more clearly understood and appreciated from a review of the following detailed description of the preferred embodiments and appended claims, and by reference to the accompanying drawings.

BRIEF DESCRIPTION OF THE DRAWINGS

To facilitate understanding, identical reference numerals have been used, where possible, to designate identical elements that are common to the figures.

DETAILED DESCRIPTION OF THE INVENTION

In the following description, various aspects of the present invention will be described. For purposes of explanation, specific configurations and details are set forth in order to provide a thorough understanding of the present invention. However, it will also be apparent to one skilled in the art that the present invention may be practiced without the specific details presented herein. Furthermore, well-known features may be omitted or simplified in order not to obscure the present invention.

During a typical examination of a body lumen, the in vivo camera system captures a large number of images. The images can be analyzed individually, or sequentially, as frames of a video sequence. An individual image or frame without context has limited value. Some contextual information is frequently available prior to or during the image collection process; other contextual information can be gathered or generated as the images are processed after data collection. Any contextual information will be referred to as metadata. Metadata is analogous to the image header data that accompanies many digital image files.

Figure 1:
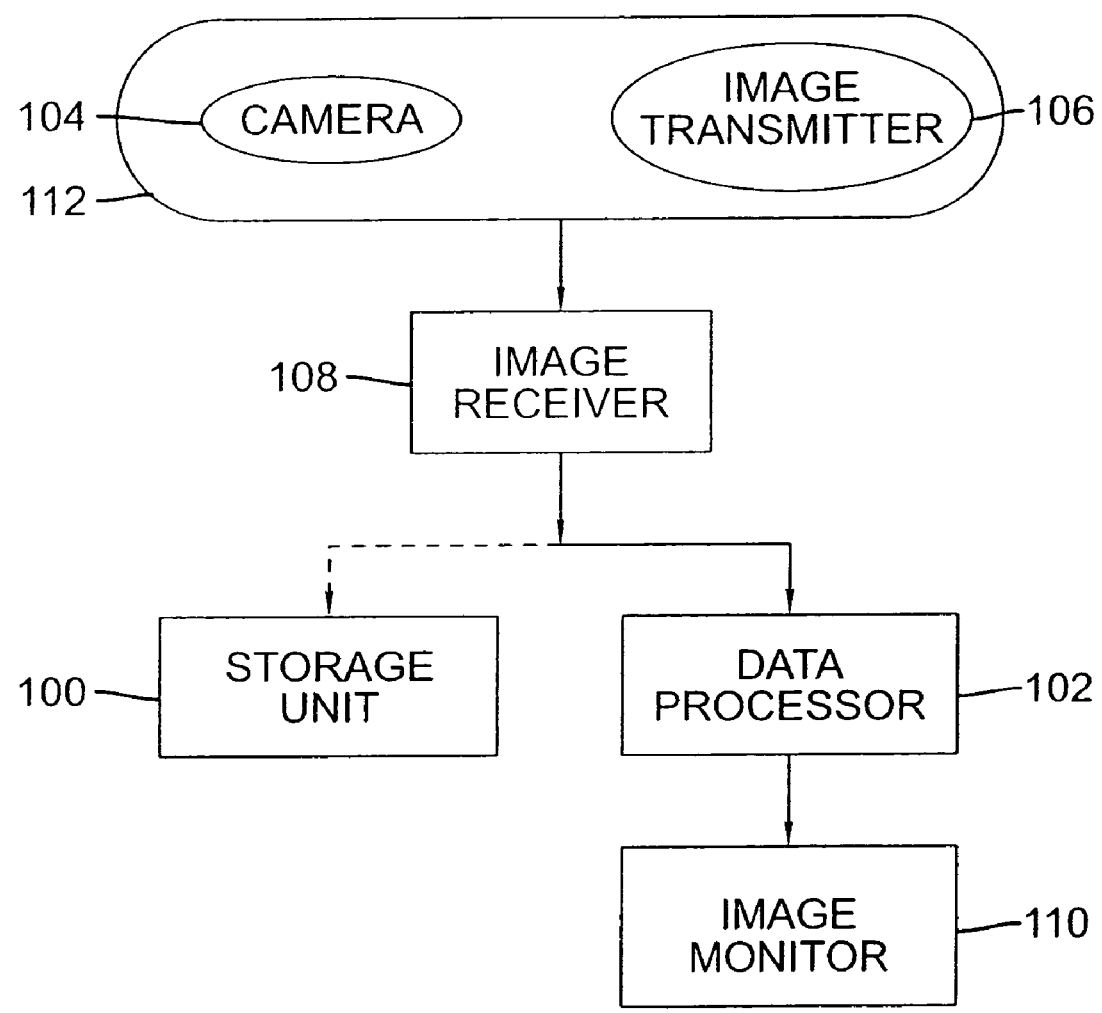
FIG. 1 (PRIOR ART) is a block diagram of an in vivo video camera system.
Figure 2:
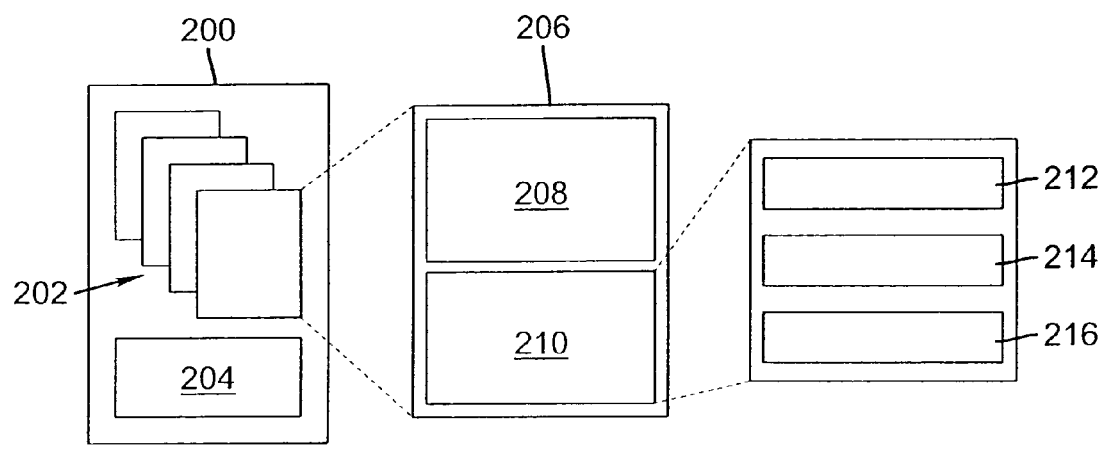
FIG. 2 is an illustration of an examination bundle.

Referring to FIG. 2, the complete set of all images captured during the examination, along with any corresponding metadata, will be referred to as an examination bundle 200. The examination bundle 200 consists of a collection of image packets 202 and a section containing general metadata 204.

An image packet 206 comprises two sections: the pixel data 208 of an image that has been captured by the in vivo camera system, and image specific metadata 210. The image specific metadata 210 can be further refined into image specific collection data 212, image specific physical data 214 and inferred image specific data 216. Image specific collection data 212 contains information such as the frame index number, frame capture rate, frame capture time, and frame exposure level. Image specific physical data 214 contains information such as the relative position of the capsule when the image was captured, the distance traveled from the position of initial image capture, the instantaneous velocity of the capsule, capsule orientation, and non-image sensed characteristics such as pH, pressure, temperature, and impedance. Inferred image specific data 216 includes location and description of detected abnormalities within the image, and any pathologies that have been identified. This data can be obtained either from a physician or by automated methods.

The general metadata 204 contains such information as the date of the examination, the patient identification, the name or identification of the referring physician, the purpose of the examination, suspected abnormalities and/or diagnosis, and any information pertinent to the examination bundle 200. It can also include general image information such as image storage format (e.g., TIFF or JPEG), number of lines, and number of pixels per line. It will be understood and appreciated that the order and specific contents of the general metadata or image specific metadata may vary without changing the functionality of the examination bundle.

Figure 3A:
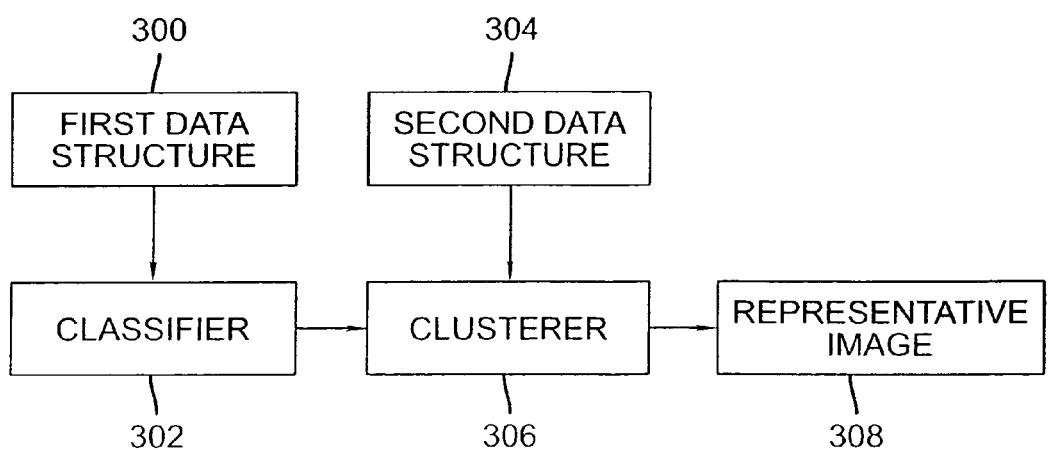
FIG. 3A is an exemplary block diagram illustration of the image indexer according to the present invention.

The present invention describes a method and system of indexing a plurality of images. FIG. 3A illustrates an image indexing system, called an image indexer. The image indexer provides a first data structure 300 for subsequent classification of the one or more images. The first data structure includes characteristics for at least one class. Using the first data structure 300, a classifier 302 classifies one or more images from the plurality of images. The image indexer also provides a second data structure 304 for subsequent clustering of the plurality of images. The second data structure 304 includes at least two sequential events in a set of known events. Using the second data structure 304, the clusterer 306 clusters the classified images. Finally, for each cluster of classified images, a representative image 308 is selected.

Figure 3B:
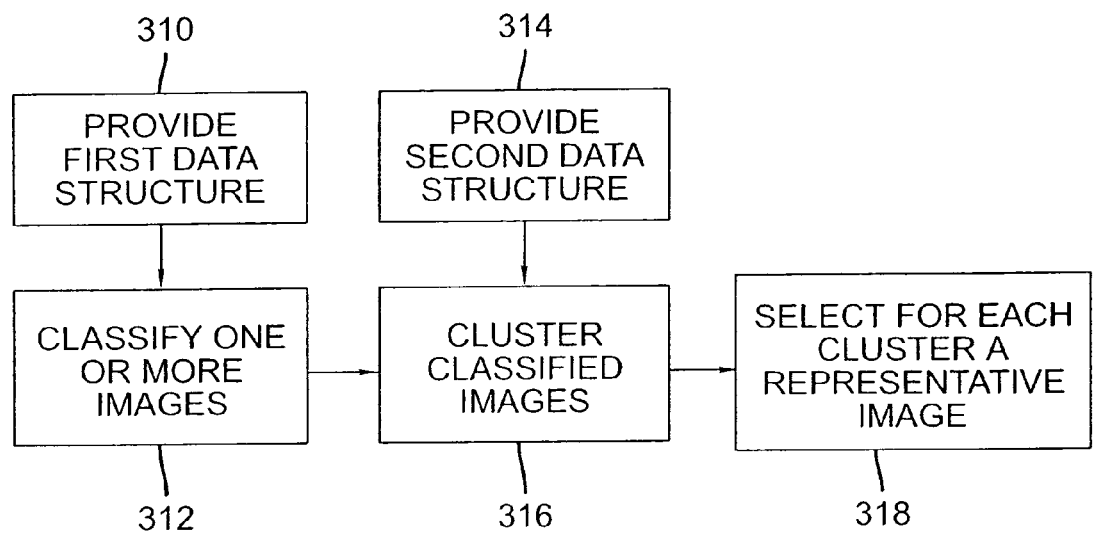
FIG. 3B shows steps for an exemplary method of indexing a plurality of images, according to the present invention.

FIG. 3B illustrates a method for indexing a plurality of images. The image indexer provides 310 a first data structure for subsequent classification of the one or more images. The first data structure includes characteristics for at least one class. Using the first data structure, the image indexer classifies 312 one or more images from the plurality of images. The image indexer also provides 314 a second data structure for subsequent clustering of the plurality of images. The second data structure includes at least two sequential events in a set of known events. Using the second data structure, the image indexer clusters 316 the classified images. Finally, the image indexer selects 318, for each cluster of classified images, a representative image.

Figure 4:
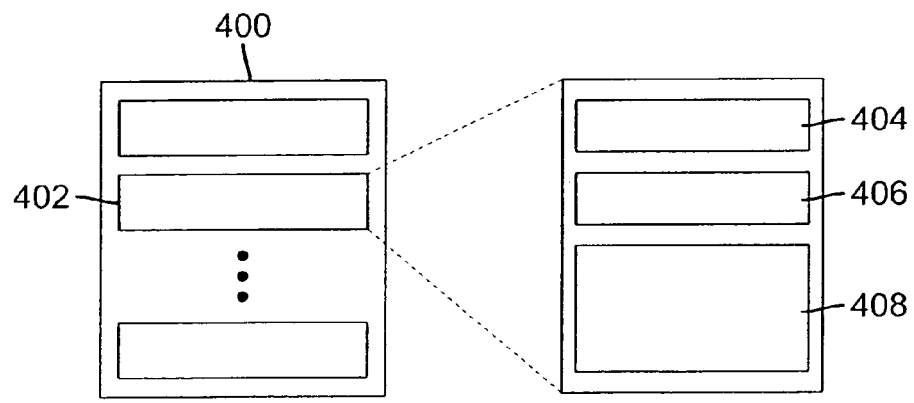
FIG. 4 is an illustration of a GI atlas.

In the preferred embodiment of the present invention, the plurality of images is contained within an examination bundle, as described in FIG. 2. Referring now to FIG. 4, a data structure known as a GI atlas 400 is defined to be a list of anatomical structures along with any pertinent characterization data for each individual anatomical structure. In the preferred embodiment, the list of anatomical structures includes the mouth, pharynx, esophagus, cardiac orifice, stomach, pylorus, duodenum, jejunum, ileum, ileocecal valve, cecum, colon, rectum, and anus. This list is not restrictive, however; other embodiments may include a subset of these anatomical structures, a more detailed set of anatomical structures, or a combination of structures (e.g., small intestine instead of duodenum, jejunum, and ileum). For a specific anatomical structure 402, pertinent characterization data may include a structure label 404, non-image specific characterization data 406, and image specific characterization data 408. The structure label can simply be the anatomical name of the structure, such as mouth, pharynx, etc., or an index or key denoting the structure. Characterization data can include any type of data that describes or characterizes the anatomical structure. For example, non-image specific characterization data 406 can include the average length or size of the structure, average relative position of the structure along the GI tract and/or with respect to other anatomical structures, average pH, temperature, and pressure levels of the structure, average motility characteristics of the structure, etc. Image specific characterization data 408 can include representative images of the anatomical structure captured from various positions and orientations, and from various illumination levels, color and/or texture distributions or features of representative images of the structure, etc., all describing spatial characteristics of the structure. In addition to, or alternatively, image specific characterization data may include temporal features found in a representative sequence of images of the object. Such features may indicate the change in physical processes over time, or the motility of the capsule. Characterization data is not limited to the specific types of data described herein; rather, any data deemed pertinent to the identification of anatomical structure can be included in the non-image specific or image specific characterization data. Furthermore, characterization data is generally predetermined, i.e., determined prior to the in vivo examination of a patient; however, it can be supplied following examination.

In a preferred embodiment of the present invention, the image indexer provides 310 the GI atlas 400 as the first data structure to classify one or more of the images from the examination bundle (i.e., a plurality of images) according to anatomical structure. This classification step 312 can be performed according to the method described in the aforementioned U.S. patent application Ser. No. 10/812,785. The GI atlas also serves as the second data structure 314 that is provided for subsequent clustering of the images from the examination bundle, as long as the GI atlas contains at least two anatomical structures that are related sequentially. This can be achieved by ordering the anatomical structures in the GI atlas in the same order that they would be traversed by traveling through the human digestive tract.

In clustering step 316, wherein the classified images use the second data structure, the clustering comprises determining a set of boundaries that partition the plurality of images into sequential events from the known set of events. Mathematically, clustering can be described in the following manner. Let $C=\{0, 1, \ldots, m\}$ be a set of class labels that index sequential events in the set of known events, $I=\{0, 1, \ldots, n\}$ be an index into the set of the plurality of images, and $\hat{I}=\{0, 1, \ldots, \hat{n}\} \subseteq I$ be an index into the set of classified images. Since each classified image must belong to the set of the plurality of images, there exists an injection $\phi: \hat{I} \to I$. Clustering comprises determining a set of boundaries $\beta_j$, $j \in \{0, 1, \ldots m+1\}$, that partition I into m+1 distinct subsets. Therefore, $\beta_0 = 0$, $\beta_{m+1} = n$, and $\beta_{j+1} > \beta_j$ $\forall j \in C$. Define $X_i \in C$ to be the class of the $i^{th}$ classified image, as determined in classification step 312, and define the vector $X = [X_i]_{i \in \hat{I}}$.

Figure 5A:
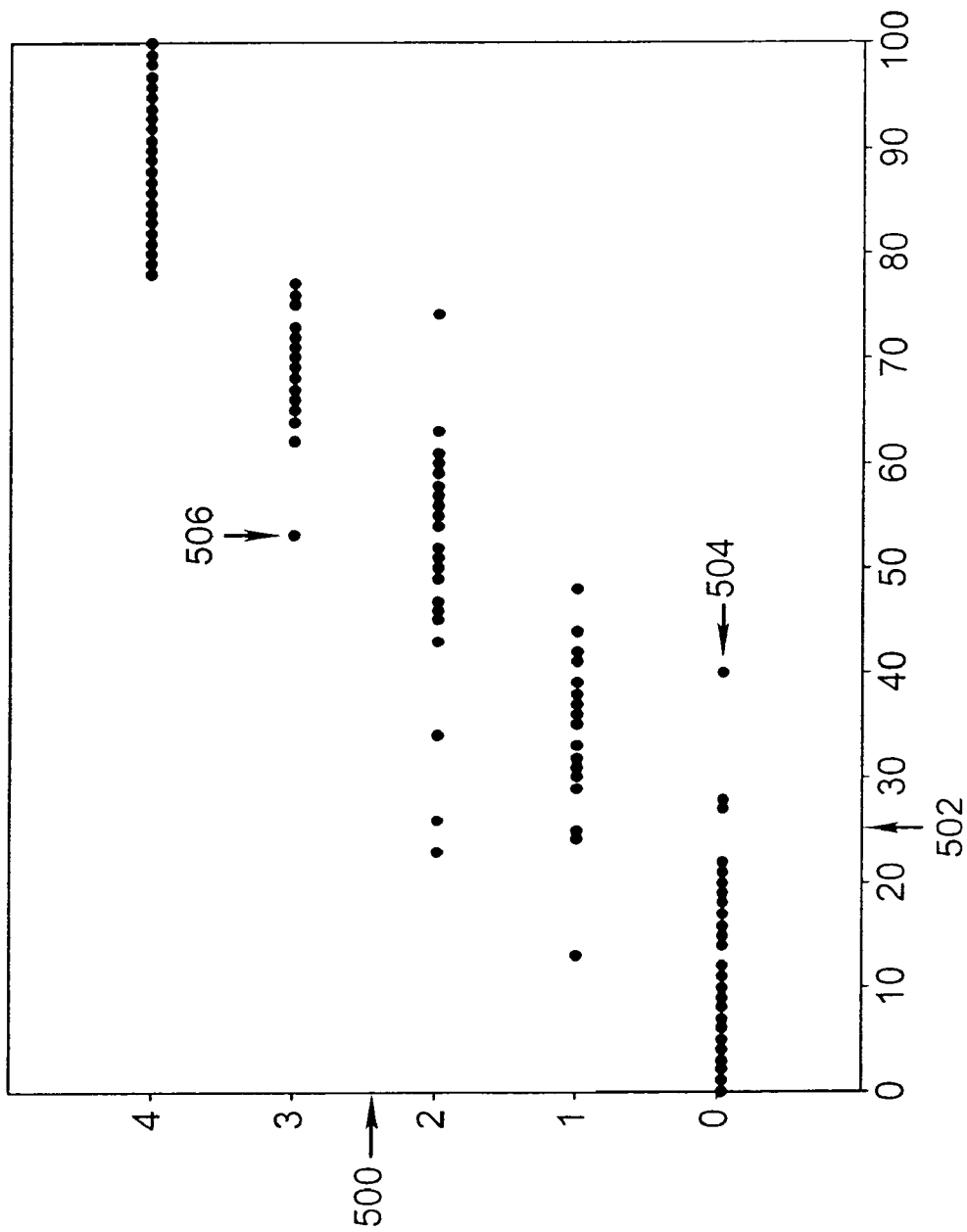
FIG. 5A is an illustration of a simulated vector of classification values of a plurality of classified images.

Depending on the accuracy of the classifier used in classification step 312, one or more of the classified images may actually be misclassified. For example, FIG. 5A illustrates the values of a simulated vector X with $n=\hat{n}=100$ (every image in the plurality of images has been classified) and $m=4$. The values of the vector (the set of class labels) are listed on the vertical axis 500, and the index of vector elements is listed on the horizontal axis 502. If events happen sequentially, as they would if X denoted the true classification of images from an examination bundle, given that the class labels indicate images of the esophagus, stomach, small intestine, large intestine, and colon, and if the classification step 312 were perfect, one would expect the values of the elements of X to be nondecreasing. Practically speaking, however, the classification step 312 will not be perfect, so some images may end up being misclassified. As an example in FIG. 5A, the element 504 appears to be incorrectly classified as belonging to class 0, and the element 506 appears to be incorrectly classified as belonging to class 3.

Figure 5B:
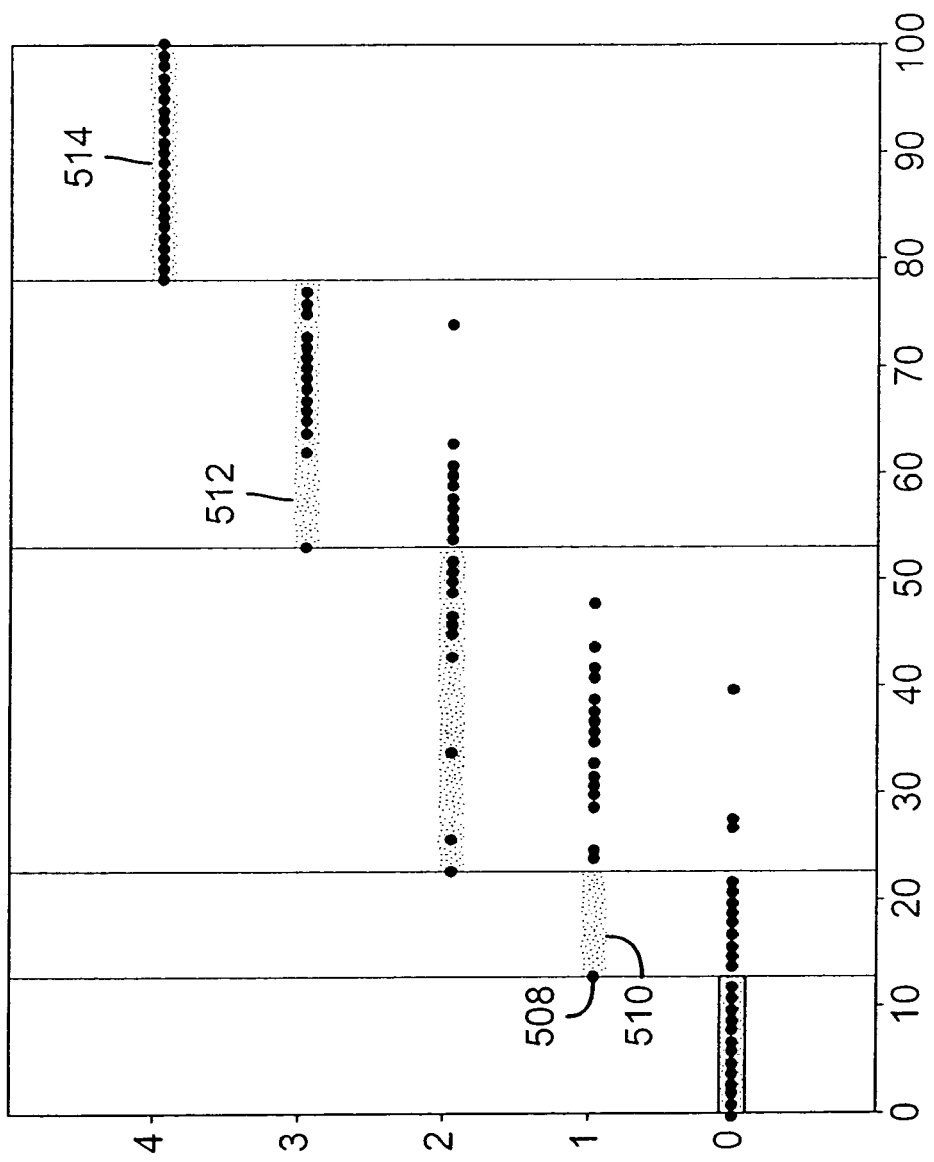
FIGS. 5B and 5C are illustrations of clusters and cluster boundaries of a simulated vector of classification values of a plurality of classified images.

One simplistic way to approach clustering is to define $\beta_j$ as the first instance of class j. Mathematically speaking, this approach defines the boundaries as $\beta_0 = 0$, $\beta_{m+1} = n$, and $\beta_k = \min\{i | X_i = k\}$, $k \in \{1, 2, \ldots, m\}$. This clustering approach is not robust to misclassification errors, as can be seen in FIG. 5B. The vertical lines indicate the boundaries between clusters, and the widths of the rectangular gray patches indicate the extent of the clusters. It is reasonable to assume that element 508 has been misclassified. This misclassification has caused the clustering approach to classify all elements of the vector within the extent of cluster 510 to be assigned to class 1, even though they clearly belong to class 0. The cluster 512 does appear to contain all of the elements that actually belong to class 3, but also appears to contain a number of elements that actually belong to class 2. In this figure, the only cluster that appears to have the appropriate boundaries is cluster 514, which appears to contain all of the elements that actually belong to class 4, and none of the elements that do not.

An alternative approach to clustering is to minimize an objective function that is constructed to measure some function of the error inherent in clustering according to a certain set of boundaries. The set of boundaries for which the objective function achieves its minimum value is considered to be the optimal set of boundaries for clustering. Defining $\theta_\beta(i)$ to be the cluster to which the $i^{th}$ classified image is assigned, i.e., $\theta_\beta(i) = j$, $\beta_j \leq i < \beta_{j+1}$, allows us to construct an objective function of the form:

$$f(\beta, X) = \sum_{i=0}^{n} \rho(X_i, \theta_\beta(i)). \tag{1}$$

Equation (1) measures the sum of a function $\rho$ of the errors inherent in clustering according to the set of boundaries $\beta_j$, $j \in \{0, 1, \ldots m+1\}$. (It is well known in the art to express objective functions alternatively as averages, medians, or other statistics of the function $\rho$ of the errors.)

The function $\rho$ can take on many forms. A simple example is $$\rho(x, y) = \begin{cases} 0, & y = x \\ 1, & y \neq x \end{cases}. \tag{2}$$

This choice of $\rho$ yields the same weight to any type of misclassification. Another example is:

$$\rho(x,y) = \|x-y\|_p^p, \tag{3}$$

where $\|\bullet\|_p$ indicates the Euclidean p-norm. The case $p=1$ defines misclassification error as the difference in class labels. For all values of p, equation (3) weights multiple-class errors higher than single-class errors. (This may or may not be appropriate.) The case $p=2$ turns equation (1) into a linear sum of squares, which can be subsequently minimized via a number of known algorithms. If the classifier used in step 312 returns not only an image classification, but also an estimated probability that the image can be classified according to each class, the estimated probabilities can be utilized in the objective function by defining $\rho$ by:

$$\rho(X_i, \theta_\beta(i)) = Pr\{X_i \neq \theta_\beta(i)\}, \tag{4}$$

where $Pr\{X_i \neq \theta_\beta(i)\}$ is the probability that the $i^{th}$ image does not belong to the class $\theta_\beta(i)$. In situations where accurate clustering is more important in certain areas than others, or for certain clusters than others, $\rho$ may alternatively be constructed to have weighting factors depending on i, $X_i$, or $\theta_\beta(i)$.

Once the objective function has been defined, the optimal boundaries for clustering can be determined by finding the set of boundaries $\beta_j$, $j \in \{0, 1, \ldots, m+1\}$, that minimize the objective function. Many techniques are known in the art for minimizing an objective function; for an overview of local optimization techniques, see R. Fletcher, *Practical Methods of Optimization*, $2^{nd}$ Ed., John Wiley & Sons, 1987. Local optimization techniques can efficiently find minima of the objective function; however, those minima may only be minima in the local sense (i.e., there may be other minima with lower objective function values outside the neighborhood of the current minimum). Another concern with many local optimization techniques is that they require an initial estimate, or guess, of the solution. Depending on the particular optimization technique and objective function, an initial estimate that is not sufficiently close to the actual minimum may cause the optimization technique to fail to converge to that minimum.

Figure 5C:
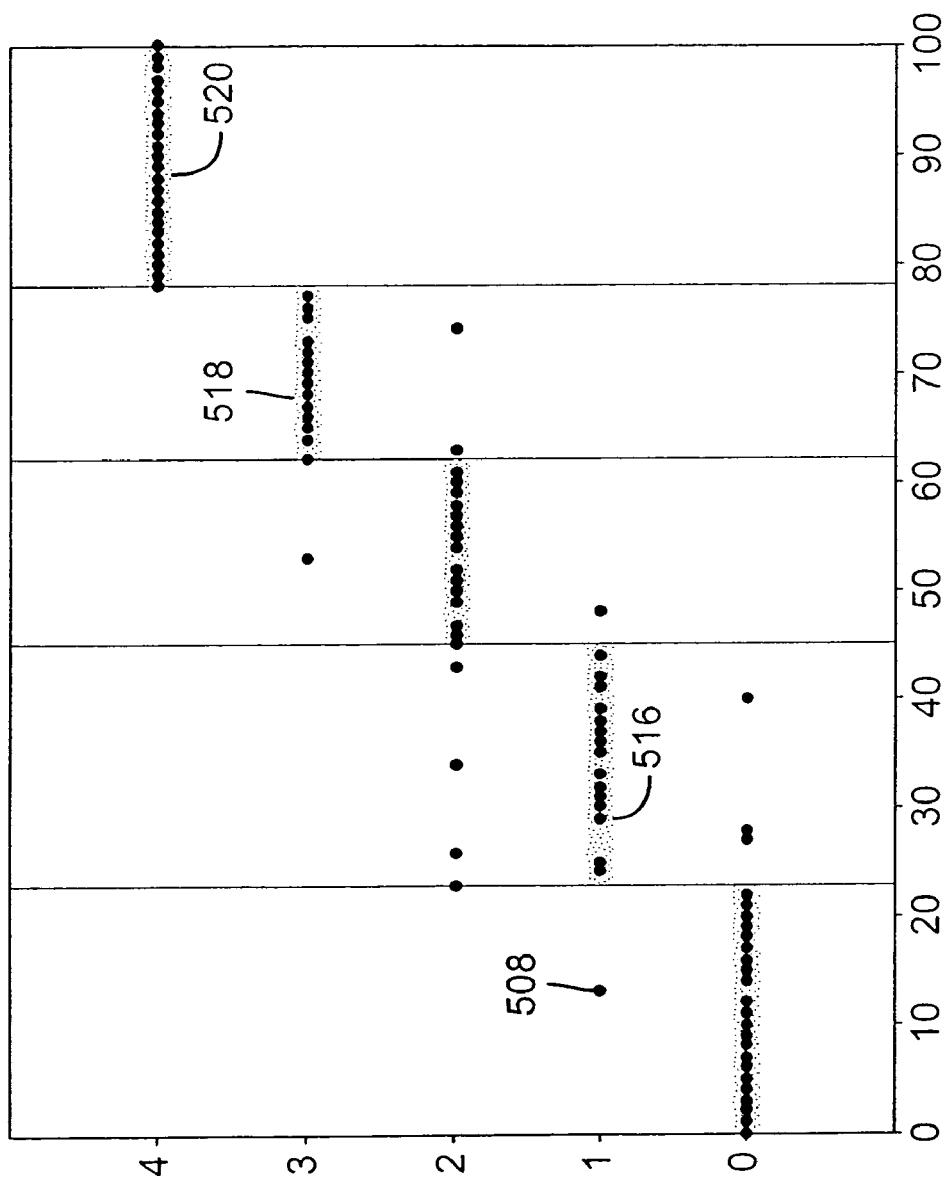

FIG. 5C illustrates the clusters determined by applying a local optimization approach to find the minimum of equation (1) with $\rho$ defined by the Euclidean 1-norm as in equation (3), using the same data as was used in FIGS. 5A and 5B. As can be seen, clusters 516 and 518 appear to describe more adequately the actual clusters in the data than do clusters 510 and 512 from FIG. 5B. Cluster 520 does not appear to have changed from cluster 514. Recall that cluster 514 appeared to adequately support the data. This evidence combined with the fact that the misclassified element 508 did not yield an incorrect boundary, illustrates that the optimization approach to clustering is more robust to misclassification errors than the approach used in FIG. 5B.

In some scenarios, extra information about the problem may be used to aid in the determination of an initial estimate of the solution. In the preferred embodiment, the initial estimate of the solution is formed using non-image specific characterization data 406 from the GI atlas 400, such as the average length or size of each anatomical structure, or the average relative positions of the anatomical structures along the GI tract and/or with respect to other anatomical structures. For example, consider an embodiment where the GI atlas 400 contains the following anatomical structures: esophagus, stomach, small intestine, and large intestine, and that the non-image specific characterization data 406 for this GI atlas contains the following information on average lengths of the structures: esophagus, 9.5 inches; stomach, 8.2 inches; small intestine, 276 inches; and large intestine, 59 inches. Assuming 50,000 in vivo images have been captured and are indexed from zero to 49,999, an initial estimate of cluster boundaries can be found by scaling the average lengths of each structure to the index set. As a fraction of the entire length of the GI tract, the anatomical structures have relative lengths: esophagus, 0.0269; stomach, 0.0232; small intestine, 0.7825; and large intestine: 0.1674. Scaling these relative lengths to a 50,000 frame image sequence, that an initial estimate of the cluster boundaries is given by: $\beta_0=0$, $\beta_1=1346$, $\beta_2=2509$, $\beta_3=41635$, and $\beta_4=49999$. Another alternative in providing initial estimates of the cluster boundaries is to take the estimates from the cluster boundaries that have been determined for previous exams of other patients, or from previous exams of the same patient.

In another embodiment, motility information is used to provide an initial estimate of the cluster boundaries. Motility can change in different portions of the GI tract due to normal peristalsis, due to the passage from one anatomical structure to another, or due to pathological conditions such as obstructions or blockages. The motility of an in vivo capsule can be measured in a variety of ways. Glukhovsky, Meron and Zinati (U.S. patent application Ser. No. 10/175,148, filed Jun. 20, 2002) describe a technique for deriving motility information based on the comparison of sequential in vivo images; a large variance in sequential images indicates a high motility rate, and a small variance indicates a low motility rate. Alternatively, motility can be measured by integrating the output of an accelerometer located in the in vivo capsule, or by differentiating the location signal along the path length, if the location of the capsule can be determined. (One way of determining the location of an in vivo capsule is described in Frisch, Glukhovsky and Levy, U.S. patent application Ser. No. 10/150,018, filed May 20, 2002.)

Figure 6:
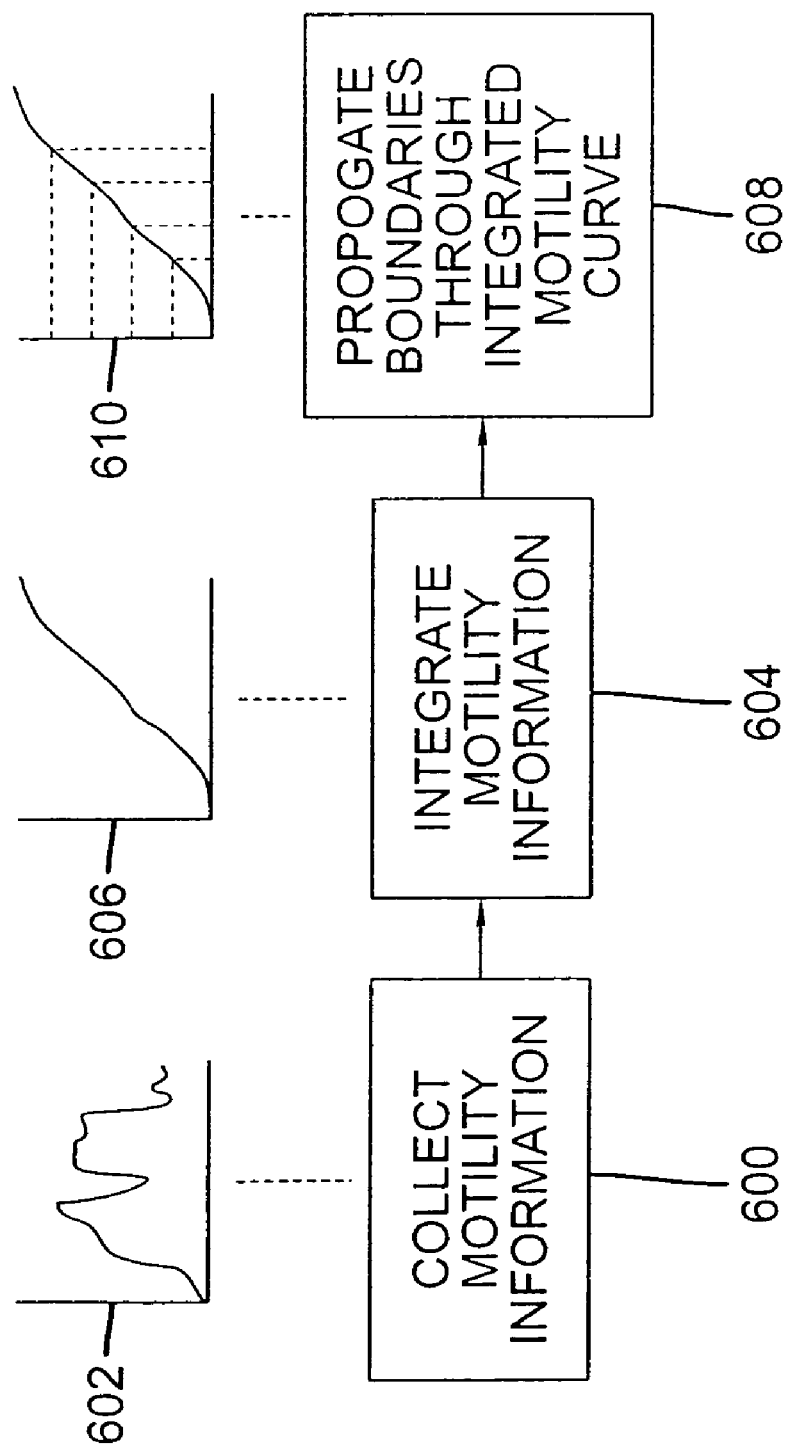
FIG. 6 is an illustration of an embodiment of the step of determining an initial estimate of cluster boundaries; and, FIG. 7 is an illustration of an embodiment of the clustering step of the current invention.

FIG. 6 illustrates a technique that utilizes motility information to provide an initial estimate of cluster boundaries. First, in step 600, motility information is collected. Motility information can be collected using any of the aforementioned techniques. The collected motility information represents the speed at which the in vivo capsule traverses the GI tract. An example plot of motility (vertical axis) versus image frame index (horizontal axis) is given by 602. Once the motility information has been collected, it is integrated in step 604 to form a curve representing distance traversed versus image frame index, as illustrated by 606. (If motility information is collected by integrating location information, as in the location information captured by the aforementioned U.S. patent application Ser. No. 10/150,018, the location information can be used directly as the output of step 604. There is no need to differentiate location information, only to subsequently integrate the result.) Once the integrated motility information has been computed in step 604, an estimate of average distances of anatomical structures can be used to construct boundaries that can be propagated (step 608) through the integrated motility curve to identify an initial estimate of boundary frames. This is illustrated by 610, where boundary estimates taken from average structure lengths on the vertical axis are propagated through the integrated motility curve to find their abscissae, yielding the initial estimate of boundary frames.

As previously mentioned, aside from the issue of determining an initial estimate of the solution, clustering approaches based on local optimization may fail to find the global minimum of the objective function. They may instead yield a minimum that is optimal within some neighborhood, but not over the entire space of possible cluster boundaries. The danger of this happening is magnified as the distance from the initial estimate to the global minimum increases. Therefore, in another embodiment of the present invention, a global optimization approach is used to find the global minimum of the objective function. For an overview of global optimization techniques, see N. Cahill, *Global Optimization: Techniques and Applications*, Master's Thesis, Rochester Institute of Technology, May 2000. Simpler global optimization techniques include pure random, adaptive random, and multistart searches. Pure random and adaptive random searches establish rules for randomly searching parameter configurations to stochastically identify the global minimum. Multistart searches entail seeding local optimization techniques with a variety of initial estimates of the solution, and then returning as the global minimum the best of the local minima. Other more complex global optimization techniques are based on models of natural/physical phenomena; such techniques include the Metropolis algorithm, simulated annealing, and the genetic algorithm.

The simulated annealing approach for global optimization is described in further detail, and is presented within an embodiment of the present invention. Since being introduced by Kirkpatrick, Gelatt, and Vecchi ("Optimization by Simulated Annealing," *Science,* 220(4598):671-680, May 13, 1983) and Cerny ("Thermodynamical Approach to the Travelling Salesman Problem: An Efficient Simulation Algorithm," *J. Opt. Theo. Applns.,* 45:41-51, 1985), simulated annealing has quickly become one of the best general purpose Monte Carlo global optimization algorithms. It is based on the physical model of annealing, where a solid is coaxed into a minimum energy crystalline state by slowly reducing its temperature. If the temperature is reduced too quickly, metastable structures result that have higher energy than the crystalline state. The fundamental building block of simulated annealing is the Metropolis algorithm, introduced some 30 years earlier by Metropolis, Rosenbluth, Rosenbluth, Teller, and Teller ("Equation of State Calculations by Fast Computing Machines," *J. Chem. Phys.,* 21:1087-1092, 1953), which simulates the energy configuration of a thermally equilibrating solid.

When a solid is in thermal equilibrium, the probability that the solid is configured in a given energy state is governed by the Boltzmann distribution:

$$P_T(x = i) = \frac{1}{Z} e^{-E_i/T}, \tag{5}$$

where i is a state with energy $E_i$ (i can be thought of as a vector of parameters and $E_i$ the corresponding value of the objective function), Z is a partition function, and T is a parameter that acts like temperature. (Without loss of generality, the Boltzmann constant can be ignored.) When T approaches zero, the Boltzmann distribution concentrates its mass in the low energy states. In the limit, the only states with non-zero probability are the minimum-energy states.

Metropolis illustrated that a combinatorial optimization scheme similar to a stochastic iterative improvement algorithm can be constructed so that the long-term probabilities of the occurrence of energy states approach a Boltzmann distribution. The difference between the Metropolis algorithm and a stochastic iterative improvement algorithm is that Metropolis allows transitions to higher-energy states with positive probability, whereas, an iterative improvement algorithm only allows transitions to lower-energy states. Because of this, the Metropolis algorithm has the potential to "jump" out of a local minimum to explore other feasible areas of the state space. The probability that a higher energy transition is accepted is given by:

$$P_{accept}(x_{k+1} = j | x_k = i, E_j > E_i) = e^{-(E_j - E_i)/T}. \tag{6}$$

This is known as the Metropolis criteria. We can encapsulate the probability of accepting a transition to any state by:

$$A_{ij}(T) = P_{accept}(x_{k+1} = j | x_k = i) = e^{\min\{-(E_j - E_i)/T, 0\}}. \tag{7}$$

We can now state the Metropolis algorithm (note the similarities to an iterative improvement algorithm):

Metropolis Algorithm
(i) Set k=1. Choose $x^{(1)}$.
(ii) Randomly choose $x^{(k+1)} \in N_k$ (the neighborhood of one-step transitions)
(iii) Accept $x^{(k+1)}$ with probability $A_{ij}(T)$. If not accepted, set $x^{(k+1)} = x^{(k)}$.
(iv) Set k=k+1. Go to (ii).

No termination criteria are explicitly stated in the Metropolis algorithm. In practice, the algorithm can be terminated when no substantial decrease in function value has been made over the last n iterations.

One of the most difficult aspects of performing combinatorial optimization with the Metropolis algorithm is the choice of an appropriate temperature parameter. If T is too large, the stationary Boltzmann distribution may not be concentrated enough at the global minimum. If T is too small, the number of iterations required to converge to the stationary distribution can be tremendous. There is definitely a trade-off that must be made, but the decision of how to make it can be very difficult. Simulated annealing utilizes a series of Metropolis algorithms, each with smaller T, so as to converge more rapidly to a stationary distribution highly concentrated at the global minimum. In terms of the physical analogy, a solid is cooled slowly enough so that thermal equilibrium is achieved at each temperature, resulting in a minimum energy crystalline structure. Therefore, much of the success of a simulated annealing algorithm depends on the cooling schedule, or the choice of decreasing values of T.

Simulated annealing can be described by the following algorithm:

Simulated Annealing
(i) Set m=1. Choose $x^{(1)}$, $T^{(1)}$.
(ii) Run Metropolis algorithm starting at $x^{(m)}$ with $T=T^{(m)}$.
(iii) Set $x^{(m+1)}$ to be the state at which (ii) was terminated.
(iv) Generate $T^{(m+1)}$ according to cooling schedule.
(v) Set m=m+1. Go to (ii).

As was the case in the Metropolis algorithm, termination of step (ii) and overall termination of the simulated annealing algorithm can be chosen to occur by a variety of means. For example, the user could choose to perform a single iteration at step (ii) and have a large number of slowly-changing temperatures in the cooling schedule. In this case, a run of the algorithm would be a realization of an inhomogeneous Markov Chain. For another problem, the user could choose a relatively coarse cooling schedule and terminate each Metropolis algorithm after a large number of iterations.

Because the success and efficiency of simulated annealing greatly depends on the cooling schedule, it is important to pick a schedule that works well. A simple geometric schedule was proposed in the aforementioned Kirkpatrick, Gelatt, and Vecchi reference, and many variants of this method have appeared in the literature since then. The initial value of T is experimentally determined so that the acceptance ratio (ratio of acceptable transitions to possible transitions at a given point) is close to one (usually around 0.95). Then the first Metropolis algorithm is almost a random walk through the state space. New values of T are generated geometrically; i.e., $T^{(m+1)} = \alpha T^{(m)}$, with $\alpha$ typically between 0.9 and 0.99. Termination of the algorithm can occur if no substantial improvement is observed over a number of iterations.

Johnson et al. ("Optimization by Simulated Annealing: An Experimental Evaluation—Part I (Graph Partitioning)," Operations Research, 37:865-892, 1989) describe some other simple cooling schedules. Besides the geometric schedule, they describe a linear schedule, where T decreases linearly, and a logarithmic schedule, where T decreases according to:

$$T^{(m)} = \frac{C}{1 + \ln(m)}, \tag{8}$$

where C is a constant. They conclude that none of these schedules yield a dramatic advantage over the geometric schedule.

Aarts and van Laarhoven ("Simulated Annealing: an Introduction," Statistica Neerlandica, 43(1): 31-52, 1989) describe a more sophisticated cooling schedule. Like the geometric schedule, the initial value of T is determined so that the acceptance ratio is close to one. New values of T are given by the iteration:

$$T^{(m+1)} = \frac{T^{(m)}}{1 + \frac{T^{(m)} \ln(1 + \delta)}{3\sigma^{(m)}}}, \quad \delta > 0, \tag{9}$$

where $\delta$ is small and $\sigma^{(m)}$ is the standard deviation of function values found during the $m^{th}$ execution of step (ii) of the simulated annealing algorithm. If $\delta$ is sufficiently small, then succeeding Markov Chains have "nearby" stationary distributions, so the number of iterations required for each Metropolis algorithm to converge is small.

All of the previous schedules monotonically decrease the temperature. In some instances, however, it may be valuable to allow a non-monotonic schedule. Osman and Christofides ("Capacitated Clustering Problems by Hybrid Simulated Annealing and Tabu Search," *Int. Trans. Oper. Res.*, 1:317-337, 1994) describe a "strategic oscillation" in which T is repeatedly decreased according to a geometric cooling schedule until progress halts, and then increased to half of its previous initial value.

Figure 7:
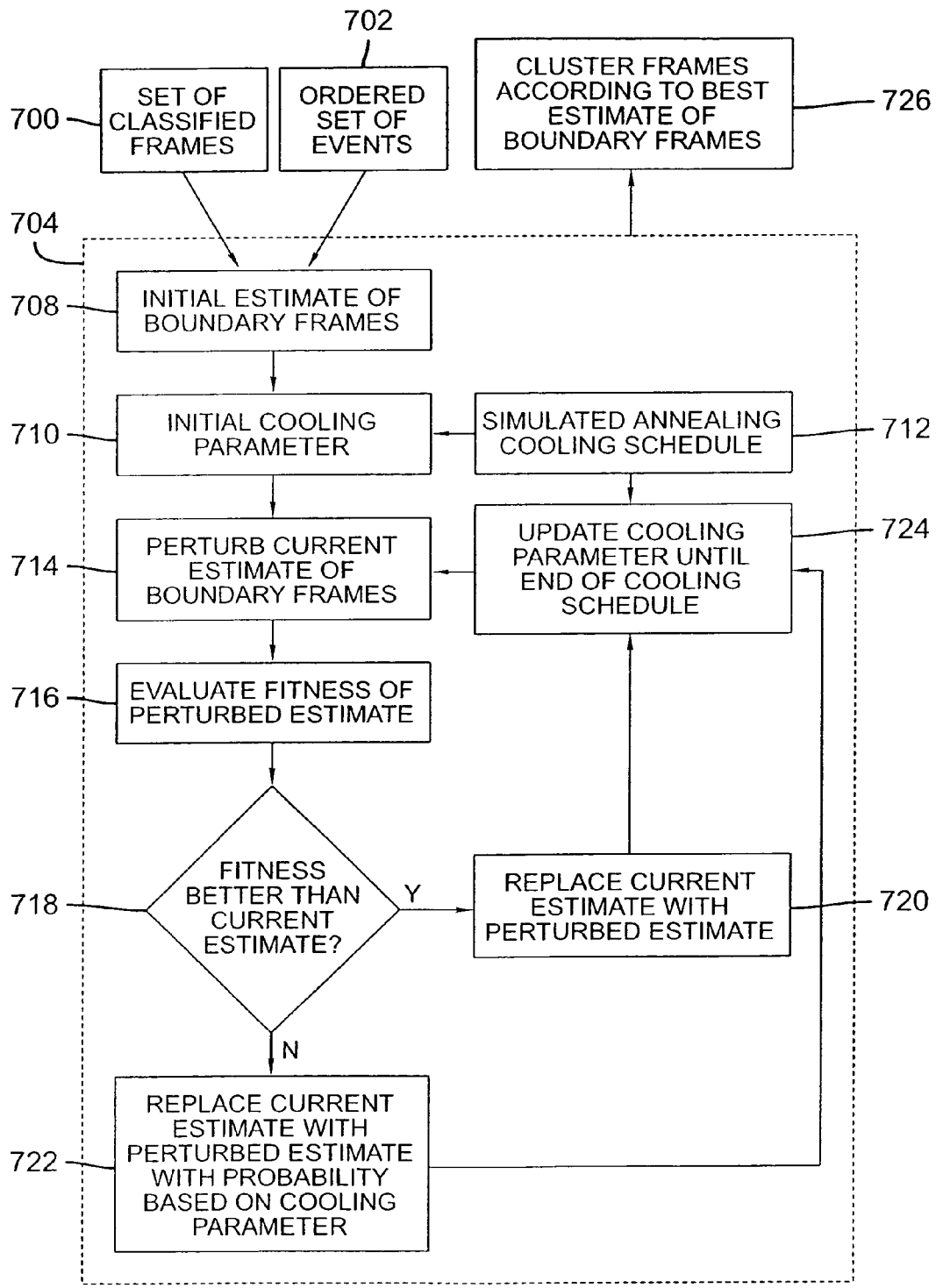

FIG. 7 is a block diagram illustrating an embodiment of the present invention that uses simulated annealing to perform the clustering step 316. A set 700 of classified frames that are generated from the classification step 312, and a data structure containing an ordered set 702 of events are provided as input to the clustering step 316. The ordered set of events 702 can be encapsulated in a GI atlas 400. Simulated annealing is used in step 704 to determine the optimal set of boundaries for clustering. First, an initial estimate 708 of boundary frames is made using the set of classified frames 700 and the ordered set of events 702. The initial estimate 708 of boundary frames can be chosen based on information provided in the non-image specific characterization data 406 of the GI atlas 400, or it can be chosen by some other means, such as by randomly selecting boundaries, or by selecting boundaries linearly spaced across the classified images. (Simulated annealing does not require that the initial estimate be close to the optimal solution.) An initial cooling parameter 710 is chosen according to an established cooling schedule 712. Then, the current estimate of the boundary frames is perturbed 714. One way that the perturbation 714 can be performed is by selecting one of the boundary frames, and randomly adding or subtracting one index position. The "fitness," or objective function value of the perturbed set of boundary frames 714 is computed in step 716, and then a query 718 is made as to whether the fitness of the perturbed set of boundary frames is better (smaller) than the fitness of the current unperturbed set of boundary frames. An affirmative response to query 718 indicates that the current estimate (the current unperturbed set of boundary frames) is replaced 720 with the perturbed set of boundary frames 714. A negative response to query 718 indicates that the current estimate (the current unperturbed set of boundary frames) is replaced 722 with the perturbed set of boundary frames 714 with probability based on the cooling parameter. The probability may be computed from $A_{ij}(T)$ of equation (7), where T is the current value of the cooling parameter. Once either step 720 or step 722 has been accomplished, the cooling parameter is updated in step 724 according to the cooling schedule 712. At this point, the simulated annealing algorithm returns to step 714 with the current estimate of boundary frames, and begins the perturbation and fitness evaluation process anew. Steps 714 through 724 are repeated until convergence, until a predetermined number of iterations has been attained, or until the cooling schedule has been completed. The optimal set of boundary frames is then used to cluster the classified images in step 726. Clustering occurs by assigning to a specific cluster any classified images whose indices are located in the interval described by the corresponding boundary frames.

The final step 318 of the image indexer is selecting, for each cluster of classified images, a representative image, or key image frame. Selecting key image frames can be done a variety of different ways. In the preferred embodiment, the first classified image belonging to each cluster (i.e., for each cluster, the image having the minimum index of all classified images in the cluster) is selected. Alternatively, for each cluster, an image can be chosen according to the image classified with the largest probability as belonging to that cluster. Alternatively, for each cluster, an image can be chosen based on user preferences, for example, to contain certain desired low-level or semantic image characteristics.

In a further embodiment of the present invention, the image indexer generates a location index of the representative images or key image frames within the plurality of images. The location index is a list of indices corresponding to images within the plurality of images that are key image frames, as found in step 318. The location index can be used for a variety of purposes, such as summarization or navigation of the plurality of images.

The invention has been described with reference to a preferred embodiment. However, it will be appreciated that variations and modifications can be effected by a person of ordinary skill in the art without departing from the scope of the invention.

PARTS LIST

| | |
|---|---|
| 100 | storage unit |
| 102 | data processor |
| 104 | camera |
| 106 | image transmitter |
| 108 | image receiver |
| 110 | image monitor |
| 112 | capsule |
| 200 | examination bundle |
| 202 | collection of image packets |
| 204 | general metadata |
| 206 | image packet |
| 208 | pixel data |
| 210 | image specific metadata |
| 212 | image specific collection data |
| 214 | image specific physical data |
| 216 | inferred image specific data |
| 300 | first data structure |
| 302 | classifier |
| 304 | second data structure |
| 306 | clusterer |
| 308 | representative image |
| 310 | operating step |
| 312 | operating step |
| 314 | operating step |
| 316 | operating step |
| 318 | operating step |
| 400 | GI atlas |
| 402 | specific anatomical structure |
| 404 | structure label |
| 406 | non-image specific characterization data |
| 408 | image specific characterization data |
| 500 | vertical axis |
| 502 | horizontal axis |
| 504 | element |
| 506 | element |
| 508 | element |
| 510 | cluster |
| 512 | cluster |
| 514 | cluster |
| 516 | cluster |
| 518 | cluster |
| 520 | cluster |
| 600 | operating step |
| 602 | plot |
| 604 | operating step |
| 606 | plot |
| 608 | operating step |
| 610 | plot |
| 700 | operating step |
| 702 | operating step |
| 704 | operating step |
| 708 | operating step |
| 710 | operating step |
| 712 | operating step |
| 714 | operating step |

-continued

| 716 | operating step |
| 718 | operating step |
| 720 | operating step |
| 722 | operating step |
| 724 | operating step |
| 726 | operating step |

What is claimed is:

1. A method for indexing a plurality of images with an image indexer, comprising:
   a) constructing in a processor a first data structure for subsequent classification of one or more images, wherein the first data structure includes characteristics for at least one class;
   b) providing by the processor an image classifier for classifying one or more individual images found in the plurality of images as classified images according to the first data structure based on an anatomical structure sequence encountered in sequential image taking events traversing an anatomical pathway;
   c) constructing in the processor a second data structure for subsequent clustering of the classified images, wherein the second data structure includes at least two sequential events in a set of known events;
   d) clustering the classified images by the processor according to the second data structure, wherein the clustering collects and integrates motility information to form an integrated motility curve and an estimate of average distances of anatomical structures is used to construct boundaries that are propagated through the integrated motility curve to identify an initial estimate of boundary frames; and
   e) selecting by the processor a representative image from each cluster of classified images.

2. The method claimed in claim 1, wherein the representative image is a key image frame found in the cluster of classified images.

3. The method claimed in claim 1, wherein the first data structure includes predetermined characteristics.

4. The method claimed in claim 3, wherein the first data structure includes spatial and/or temporal characteristics.

5. The method claimed in claim 1, further comprising constructing in the processor a location index that includes the selected representative image.

6. A method for indexing a plurality of images, comprising the steps of:
   a) providing in a processor a first data structure for subsequent classification of one or more images, wherein the first data structure includes characteristics for at least one class;
   b) classifying by the processor, according to the first data structure, one or more individual images found in the plurality of images as classified images based on an anatomical structure sequence encountered in sequential image taking events traversing an anatomical pathway;
   c) providing in the processor a second data structure for subsequent clustering of the classified images, wherein the second data structure includes at least two sequential events in a set of known events;
   d) clustering the classified images by the processor according to the second data structure, wherein the clustering collects and integrates motility information to form an integrated motility curve and an estimate of average distances of anatomical structures is used to construct boundaries that are propagated through the integrated motility curve to identify an initial estimate of boundary frames; and
   e) selecting by the processor for each cluster of classified images, a representative image.

7. The method claimed in claim 6, wherein the representative image is a key image frame found in the cluster of classified images.

8. The method claimed in claim 6, wherein the first data structure includes predetermined characteristics.

9. The method claimed in claim 8, wherein the first data structure includes spatial and/or temporal characteristics.

10. The method claimed in claim 6, further comprising the step of generating in the processor a location index of the representative images within the plurality of images.

11. An image indexer for indexing a plurality of images, comprising:
    a first data structure for subsequent classification of one or more images, wherein the first data structure includes characteristics for at least one class;
    an image classifier for classifying one or more individual images found in the plurality of images as classified images according to the first data structure;
    a second data structure for subsequent clustering of the classified images, wherein the second data structure includes at least two sequential events in a set of known events;
    a clusterer for clustering the classified images according to the second data structure; and
    a selector for selecting a representative image from each cluster of classified images,
    wherein the clusterer collects and integrates motility information to form an integrated motility curve, and
    wherein an estimate of average distances of anatomical structures is used to construct boundaries that are propagated through the integrated motility curve to identify an initial estimate of boundary frames.

12. A method for indexing a plurality of images, comprising:
    providing in a processor a first data structure for subsequent classification of one or more images, wherein the first data structure includes characteristics for at least one class;
    classifying by the processor, according to the first data structure, one or more individual images found in the plurality of images as classified images;
    providing in the processor a second data structure for subsequent clustering of the classified images, wherein the second data structure includes at least two sequential events in a set of known events;
    clustering by the processor the classified images according to the second data structure; and
    selecting by the processor for each cluster of classified images, a representative image, and
    wherein the clustering comprises simulated annealing, and the simulated annealing comprises:
    1) generating a set of classified frames from the classifying step;
    2) providing a data structure containing an ordered set of events;
    3) determining a set of boundaries for clustering using the simulated annealing;
    4) forming an initial estimate of boundary frames using the set of classified frames and the ordered set of events;
    5) choosing an initial cooling parameter according to an established cooling schedule;

6) performing perturbation on the current estimate of the boundary frames;
7) evaluating fitness of a perturbed estimate;
8) inquiring whether a fitness of the perturbed set of boundary frames is smaller than a fitness of a current unperturbed set of boundary frames;
9) replacing the current estimate with the perturbed set of boundary frames when an affirmative response to the above query is given;
10) replacing the current estimate with the perturbed estimate with probability based on a cooling parameter when a negative response to the above query is given;
11) updating the cooling parameter according to the cooling schedule;
12) performing the simulated annealing again with the current estimate of boundary frames, while beginning the perturbation and fitness evaluation steps anew;
13) repeating steps 6 through 7 until convergence, or until a predetermined number of iterations has been attained, or until the cooling schedule has been completed; and
14) using the set of boundary frames to cluster the classified images.

13. A method of forming an image indexer for indexing a plurality of in vivo images captured from an in vivo imaging system, comprising:

a) constructing a first data structure in a processor for subsequent classification of one or more in vivo images, wherein the first data structure includes anatomical structure characteristics as imaged by the in vivo imaging system;
b) providing by the processor an image classifier for classifying one or more individual images found in the plurality of in vivo images as classified in vivo images according to the first data structure based on an anatomical structure sequence encountered in sequential image taking events traversing an anatomical tract;
c) constructing a second data structure in the processor for subsequent clustering of the classified in vivo images, wherein the second data structure includes at least two sequential events in a set of known events;
d) clustering the classified in vivo images by the processor according to the second data structure, wherein the clustering collects and integrates motility information to form an integrated motility curve and an estimate of average distances of anatomical structures is used to construct boundaries that are propagated through the integrated motility curve to identify an initial estimate of boundary frames; and
e) selecting by the processor a representative image from each cluster of classified in vivo images.

\* \* \* \* \*